(12) United States Patent
Goldberg (10) Patent No.: US 11,311,640 B1
(45) Date of Patent: Apr. 26, 2022

(54) AIR STERILIZER APPARATUS AND METHOD

(71) Applicant: Blisk Corp, Hawkinsville, GA (US)

(72) Inventor: Shalom J Goldberg, Hawinksville, GA (US)

(73) Assignee: BLISK CORP, Hawkinsville, GA (US)

( * ) Notice: Subject to any disclaimer, the term of this patent is extended or adjusted under 35 U.S.C. 154(b) by 0 days.

(21) Appl. No.: 17/308,024

(22) Filed: May 4, 2021

Related U.S. Application Data (63) Continuation-in-part of application No. 17/238,205, filed on Apr. 23, 2021.

(51) Int. Cl.
*A61L 9/20* (2006.01)

(52) U.S. Cl.
CPC ............ *A61L 9/20* (2013.01); *A61L 2209/111* (2013.01); *A61L 2209/12* (2013.01); *A61L 2209/14* (2013.01)

(58) Field of Classification Search
None
See application file for complete search history.

(56) References Cited

U.S. PATENT DOCUMENTS

| | | | |
|---|---|---|---|
| 6,494,940 B1 * | 12/2002 | Hak .......................... A61L 9/16 55/471 |
| 10,905,790 B1 * | 2/2021 | Moore ................... A61M 16/06 |
| 2010/0143205 A1 * | 6/2010 | Engelhard ............... A61L 9/205 422/121 |
| 2017/0321877 A1 * | 11/2017 | Polidoro ............. F21V 33/0088 |

\* cited by examiner

*Primary Examiner* — Jelitza M Perez
(74) *Attorney, Agent, or Firm* — Steven C. Stewart (57) ABSTRACT

A method and device for sterilizing air to kill pathogens is disclosed. An elongated ultraviolet-C (UV-C) light source is placed within an elongated chamber in a housing. At least one fan directs air from an interior space into the chamber and then back out to the interior space. A controller automatically adjusts the speed of the fan to ensure that the air passes through the chamber at a predetermined flow rate such that pathogens in the air are irradiated in the chamber for a sufficient time period to be deactivated by the ultraviolet-C light source.

18 Claims, 8 Drawing Sheets

AIR STERILIZER APPARATUS AND METHOD

TECHNICAL FIELD

These claimed embodiments relate to an Air Sterilizer Device for removing pathogens from the air and more particularly to a method for sterilizing the air using Ultraviolet-C (UV-C) light.

BACKGROUND OF THE INVENTION

Numerous industries such as healthcare, foodservice, beer brewers, hospitality, public facilities, transportation services have interior areas where multiple people congregate. When multiple people congregate, they are susceptible to catching a virus or other conditions due to some of these people exhaling airborne pathogens that could be contagious (such as Covid-19 or MRCR). These pathogens have been known to cause serious illness and even death.

Ultraviolet-C (UV-C) light has been used to kill such pathogens in a closed environment. However, exposure to UV-C has harmful effect to the eyes and skin. The UV-C bulbs may be expensive and have a limited life expectancy, in addition to their consumption of power to operate. Further if a pathogen is exposed to UV-C for an insufficient time period, such pathogen could mutate and increase its resistance to UV-C making the pathogen harder to eliminate. Current UV-C systems do not adequately ensure that the pathogen is eliminated. In addition, current UV-C systems continue to operate whether or not there are pathogens present thereby consuming energy and reducing the time between a periodic replacement of the UV-C bulbs.

SUMMARY OF THE INVENTION

This application relates to an air sterilization device. In one implementation, a device for irradiating pathogens in the air of an interior space is provided. The air sterilization device includes a housing containing inner walls that form an elongated chamber with a first end and a second end. The chamber encloses an axis that extends along the chamber parallel to the chamber's inner walls. An elongated ultraviolet-C (UV-C) light source extending within the elongated chamber from the first end to the second end parallel to the axis. At least one fan direct air from outside of the housing into the chamber first end and directs air within the chamber out of the chamber second end to outside of the housing. A controller automatically adjusts the speed of the fan to ensure that the air passes through the chamber at a predetermined flow rate such that pathogens in the air are irradiated in the chamber for a sufficient time to be deactivated by the ultraviolet-C light source.

In another implementation, a method for sterilizing pathogens in the air within an outer housing that supports an inner housing having inner walls that enclose an elongated chamber with a first end and a second end and enclose an axis extending along the chamber parallel to the inner walls is disclosed. The method includes directing, with a fan, air to pass from outside of the outer housing though the chamber parallel to the axis via the first end and out of the chamber to outside of the outer housing via the second end. An elongated ultraviolet-c (UV-C) light source extending within the elongated chamber parallel to the axis irradiates air passing through the chamber. A sensor detects a flow rate of air passing though the elongated chamber. A speed of the fan is adjusted based on the detected air flow rate to ensure that pathogens in the air passing though the chamber are irradiated by the UV-C light source for a sufficient time period to become deactivated.

In a further embodiment, an apparatus for irradiating pathogens in the air is disclosed. The apparatus includes an outer housing supporting an inner housing having inner walls that form a first and a second elongated chamber. Each chamber has a first end and a second end. A first axis extends along the first chamber parallel to the inner walls and a second axis extends along the second chamber parallel to the inner walls. The second end of the first elongated chamber couples with the first end of the second elongated chambers. the first axis extends through the first elongated chamber forms an angle of at 90 degrees or less with respect to the second axis. An elongated ultraviolet-c (UV-C) light bulb extends within the first elongated chamber parallel to the first axis and another elongated ultraviolet-c (UV-C) light bulb extends within the second elongated chamber parallel to the second axis. A first fan to direct air from outside of the housing into the first chamber first end. A second fan to direct air within the first and second chamber out via the second chamber and the second chamber second end to outside of the housing such that pathogens in the air are irradiated by the UV-C light bulbs when passing through the first and second chamber.

BRIEF DESCRIPTION OF THE DRAWINGS

The detailed description is described with reference to the accompanying figures. In the figures, the left-most digit(s) of a reference number identifies the figure in which the reference number first appears. The use of the same reference number in different figures indicates similar or identical items.

DETAILED DESCRIPTION

Figure 1:
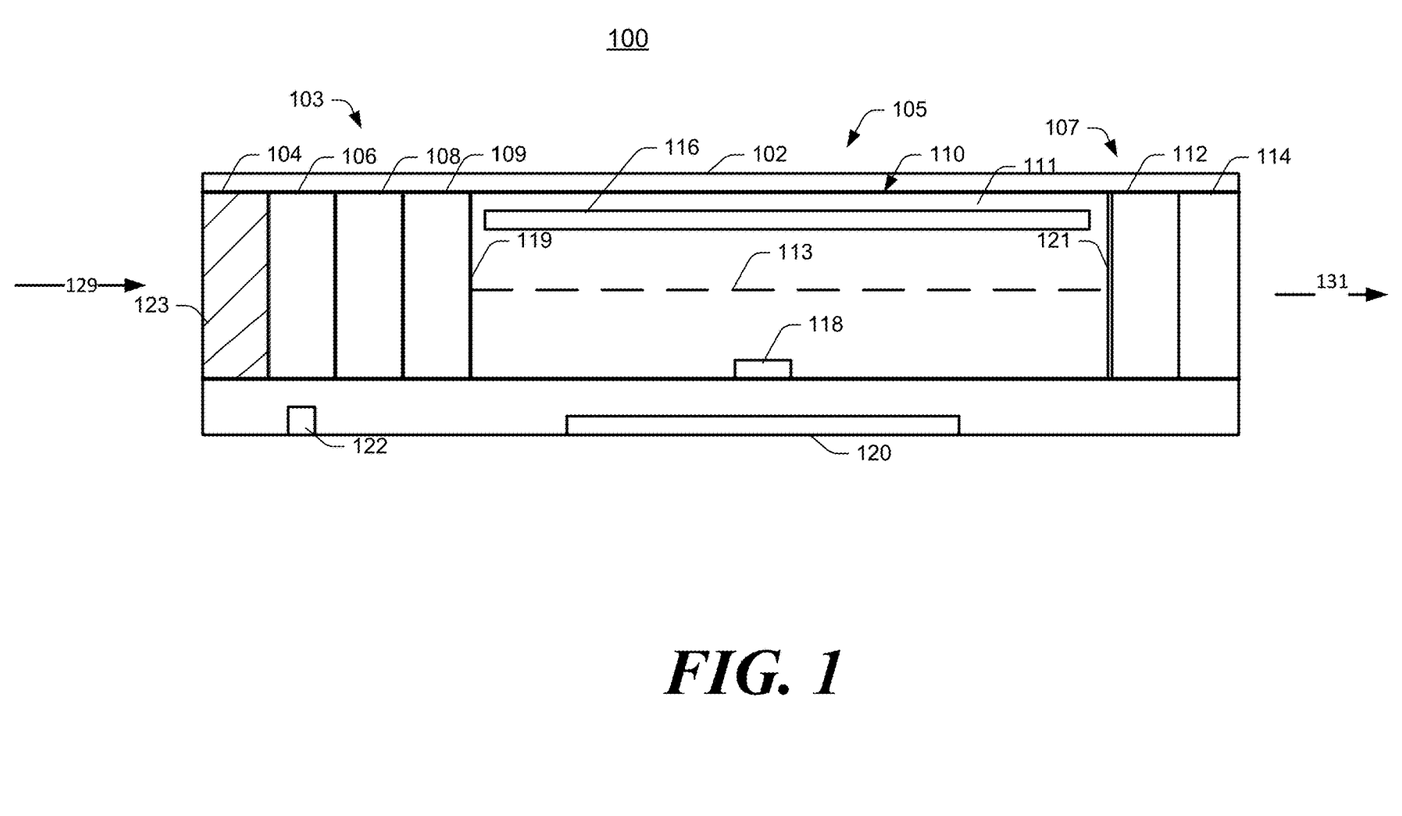
FIG. 1 is a simplified mechanical diagram illustrating parts of the air sterilization device.
Figure 2:
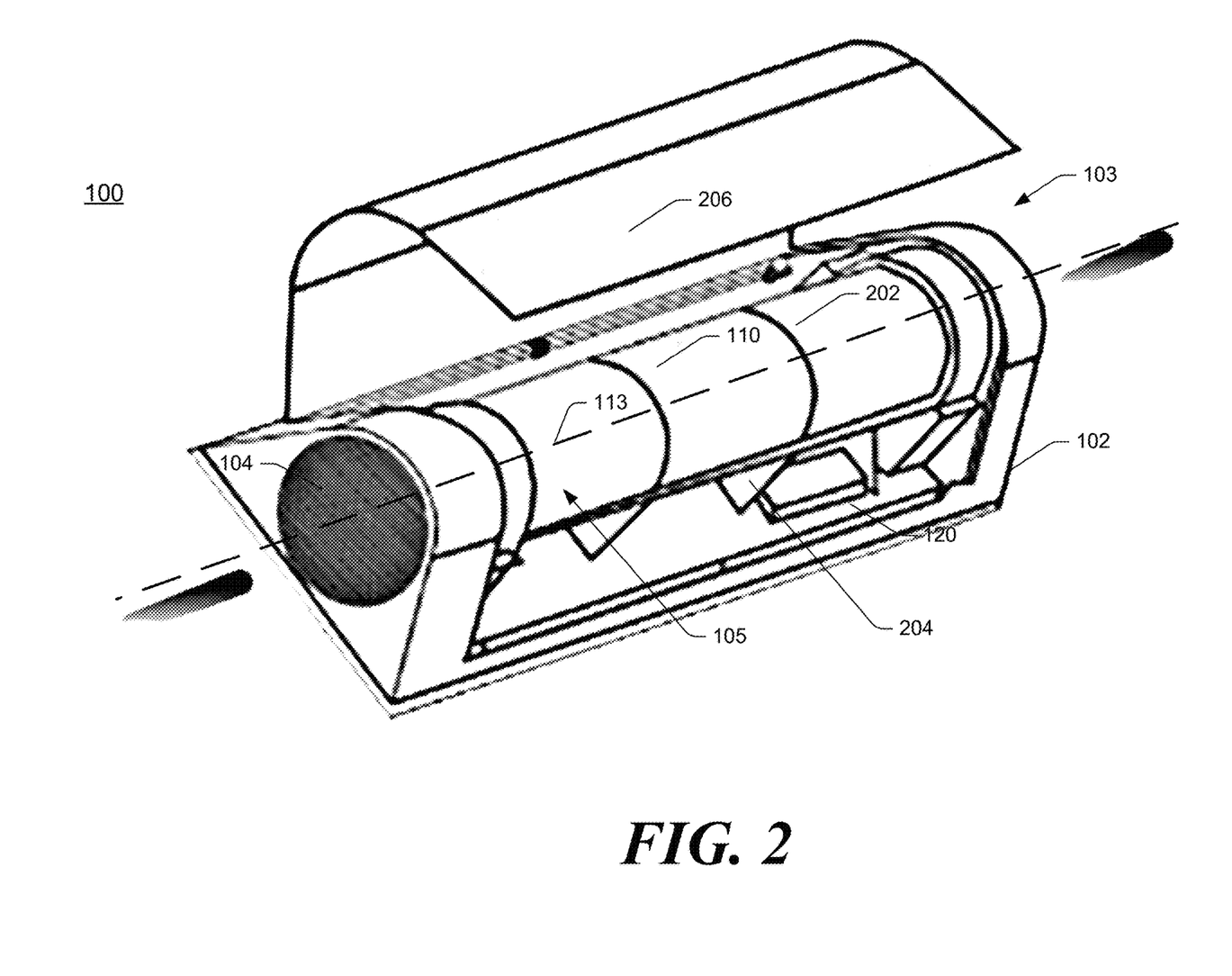
FIG. 2 is an isometric view of one embodiment of the air sterilizer device.

Referring to FIGS. 1 and 2, there is shown an air sterilization device 100 for deactivating pathogens in the air of an interior space. The air sterilization device 100 includes an outer housing 102 that contains an intake portion 103, coupled with an inner housing 105 that is coupled with an outtake portion 107. The intake portion 103 includes a trim vent 104 coupled to an air filter 106, a fan 108, and one or more light blocking (LB) vents 109. The inner housing 105 has inner walls 111 that form an elongated inner chamber 110 (preferably tubular, rectangular, or triangular shaped) with an axis extending parallel to the inner walls 111 and the length of the chamber 110. The inner walls 111 may be coated with a highly reflective surface. Chamber 110 has an axis 113 extending through it parallel to walls 111 and extends in a direction of air flow in chamber 110. The outtake portion 107 includes another LB vent 112 coupled to fan 114. Supported by one or more brackets (not shown) on the inner walls of the inner housing and extending parallel to the axis are one or more ultraviolet-c (UV-C) bulbs 116 and an air flow and/or UV-C light sensor 118. LB vents 109 and 112 are respectively disposed adjacent first end 119 and second end 121 of chamber 110 in inner housing 105 for blocking light from the UV-C bulb 116 from exiting outside of the outer housing 102.

Air filter 106 is optional and may be disposed within the outer housing 102. Air filter 106 is disposed adjacent the first end of chamber 110 to filter particles/dust from the air prior to the air entering the chamber 110.

The air sterilization device 100 includes a controller 120 mounter to the outer housing 102 and coupled with the one or more 222 nm or 256 nm ultraviolet-c (UV-C) bulbs (also referred to herein as lamps) 116. An exemplary bulb 116 may be a Far UV-C Care222® lamp produced by USHIO, Inc and arranged in an array that delivers a singular wavelength of 222 nm.

Figure 4:
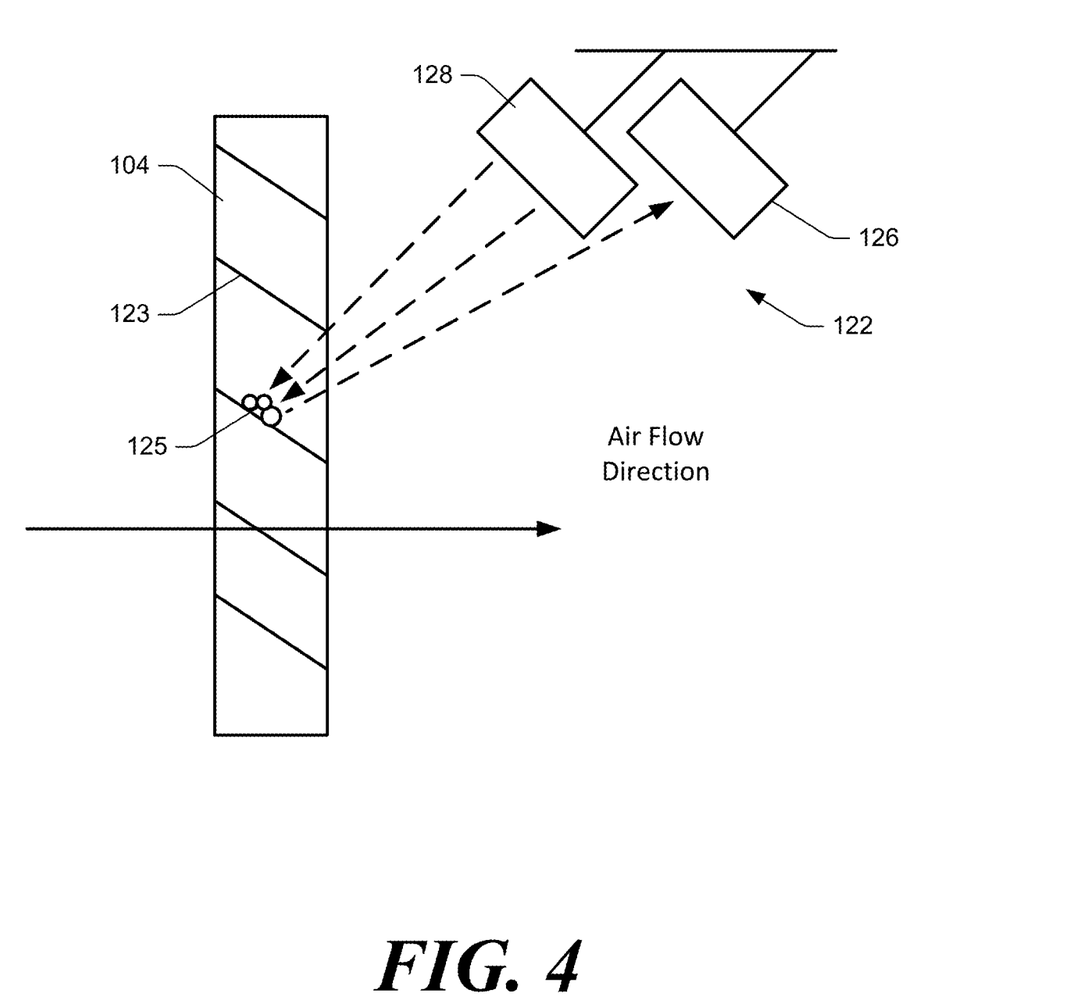
FIG. 4 is an exploded view of a transducer detecting pathogens on the trim vent shown in FIG. 1.

Referring to FIGS. 1 and 4, one or more subsonic transducers 122, each having a receptor 126 and an emitter 128, that may be mounted on wall on the inside of the outer housing 102 adjacent the trim vent 104. Trim vent 104 may include multiple flaps 123. During operation air passes over the flaps prior to entering chamber and pathogens in the air may be deposited on the flaps 123. The subsonic transducers 122 may be arranged as an array of super-sensitive 4 piezoelectric chip-based transducers designed to operate in the subsonic range. The number of receptors 126 and emitters 128 for these transducers 122 may be doubled to reinforce their modulation. Transducers 122 are directed at the flaps 123 during operation and are operable to send a sound signal that receives back patterns of various pathogens 125 (pathogen types) deposited from the air onto the flaps. The emitter 228 of transducer 122 transmits a subsonic sound and a receptor 126 receives the transmitted sound after being reflected off flaps 123. The received sound pattern may form a unique signature specific to the pathogen on the flap 123. Such signature may be identified from a library of patterns stored in a memory of the controller 120. Although the sound pattern is shown to reflect off of flaps 123, the transducer 122 may reflect its sound signal off of other parts in the air sterilizer 100 such as the LB vent 109.

Transducers 122, fans 108 and 114, and the UV-C lamp 116 are controlled by controller 120. Transducers 122 provide information regarding what was sensed to controller 120. Controller 120 may include memory that maintains a library of known pathogen types and their respective ultrasonic patterns. Upon receiving a pattern from transducers 122, controller 120 may determine the type of pathogen present in the air by comparing the received pattern against known patterns in its library. Controller 120 may then provide a signal to fans 108 and 114 to increase or decrease a predetermined time air flows through the chamber 110 to kill and/or deactivate a pathogen in the air. Such predetermined time may be set based on the determined pathogen type. (harder to kill pathogens require more time while quicker to kill pathogens require less time). One such predetermined time known to deactivate all pathogens is at least 3.2-4 seconds. In one embodiment controller 120 may turn off bulbs 116 and/or fans 108 and 114 completely if no pathogens are detected.

Controller 120 may also provide an audio indication or a visual indication using an LED (not shown) or audio speaker indicating the UV-C lamp 106 is on, or that the UV-C lamp 106 is off, and/or that the pathogen is being deactivated or killed. The controller 120 may have the results of the scan posted to its internal storage and may transmits the pathogen results wirelessly to a hand-held PDA unit or smart phone that an operator may carry or a remote database/server.

The UV-C bulbs 106 may be mounted to via the inner housing 105 to a cover panel 202 (FIG. 2) on the outer housing 102 radiate the air when passing through the chamber 110. The one or more subsonic transducers 122 may be mounted to the outer housing 102.

Air sterilization device 100 may also include an interior housing 105 with a metal skeleton 204 to hold the components, sensors (e.g. transducer 122 and air and/or uv-c light sensor 118), and lamps 116 in place permanently. Circuitry in controller 120 may be accessed through a rear panel 206 when a cover panel 202 is removed. Cover panel 202 of the Air sterilization device 100 could be detachable from interior housing 105 with a special key that a service technician will carry in order to provide servicing.

Figure 8:
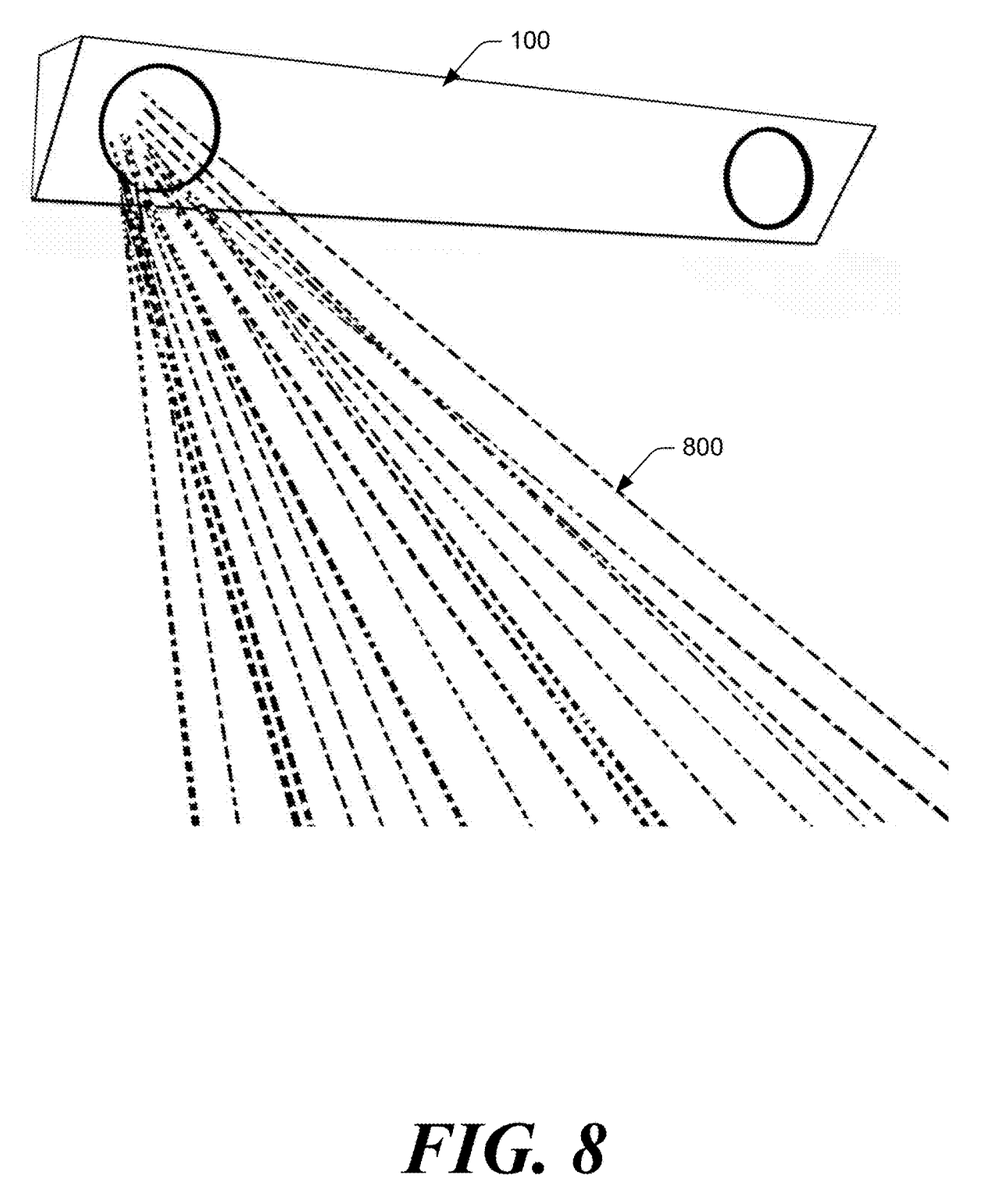
FIG. 8 is a isometric view of an air sterilization device shown a pattern of disbursement of air from the device to an interior space.

During operation fans 108 and 114 to direct air from outside of the outer housing 102 (from interior space 129) into a first end 119 of chamber 110. Fans 108 and 114 direct air within the chamber 110 out of a second end 121 of chamber 110 to outside of the outer housing to the interior space 131. Such air may be direct in a cone 800 as shown in FIG. 8. In response to the speed of the flow of air detected by sensor 118 (although speed detector sensor 118 is shown as a device disposed within chamber 110, the speed detection sensor 118 could be mounted on fan 108 or 114 or could be a device that senses current/voltage being provided to fans 108 or 114). In response to the determined speed of the air though the chamber or determined speed of fan 108 and/or 114, the controller 120 automatically adjusts the speed of fans 108 and 114 to ensure that the air passes through the chamber 110 at a predetermined flow rate (e.g., 1.2 feet per second). In addition, the chamber 110 is constructed of sufficient length (e.g. 4 feet) so that pathogens in the air passing though chamber 110 are irradiated for a sufficient time period to be deactivated by the ultraviolet-C lamp 106. Controller 120 may send a signal to the fans 108 and 114 to change the rotational fan speed of the one or more fans 108 and 114 based on the pathogen type detected, or may turn off bulb 116 if no pathogens in the air/on flap 123 are detected.

Figure 3:
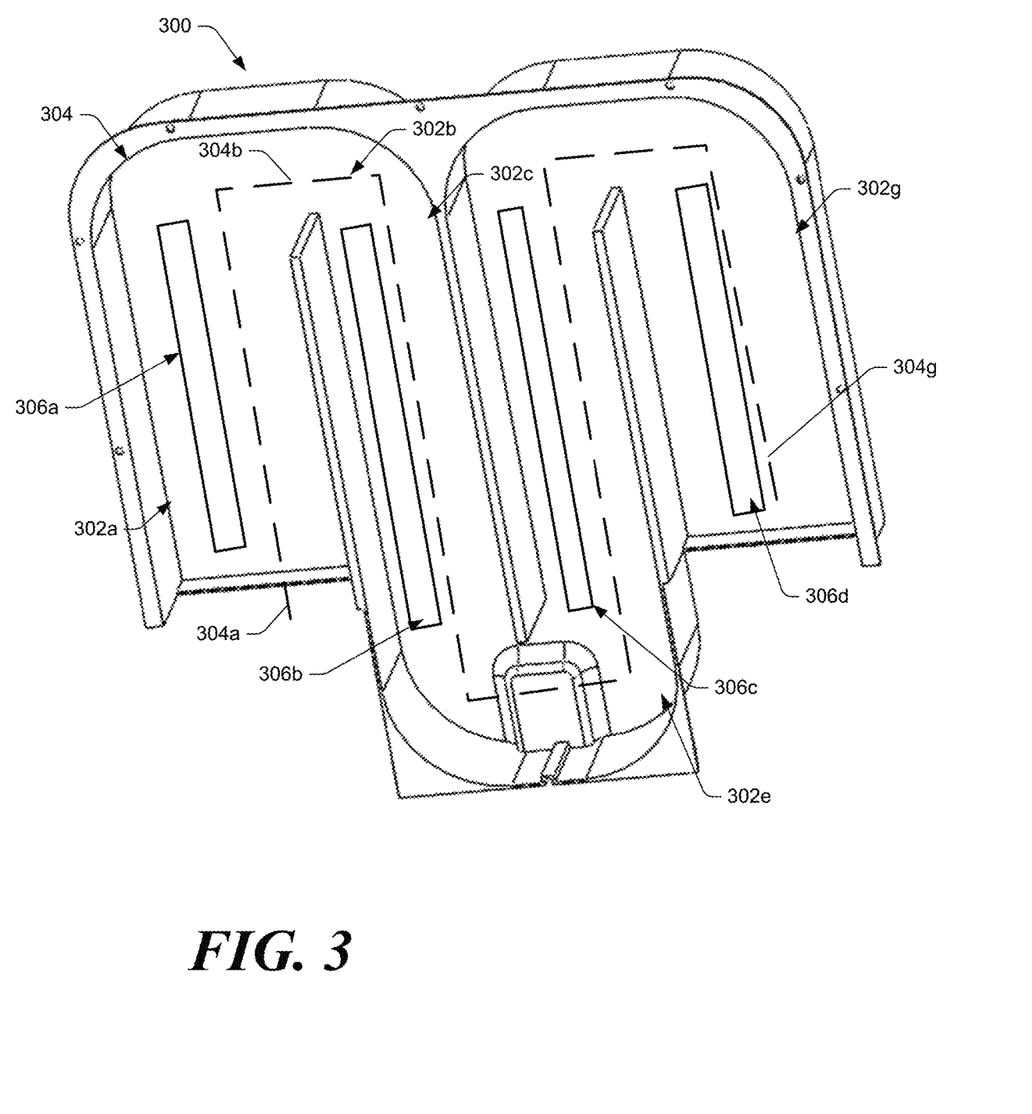
FIG. 3 is an isometric view of showing a cross section of a chamber in another embodiment of the air sterilizer device.

Referring to FIG. 3, there is shown a cross section of sterilization device 300, which is an alternate embodiment of the sterilization device 100 shown in FIG. 1. Sterilization device 300 has all the components of sterilization device 100, but the walls of the interior housing 304 within device 300 form multiple chambers 302a-302g that have a cylindrical, tubular, or rectangular cross section and is shaped in an S pattern. Each of the chambers 302a-302g couple with an adjacent chamber, e.g., chamber 302a couples with chamber 302b, and chamber 302b couples with chambers 302a and 302c, etc. Axes 304a-g each extend parallel to the wall of chamber 302a-g respectively. Axis 304a forms a 90-degree angle with respect to axis 304b, and each subsequent axis forms at least a 90-degree angle with respect to the previous axis to form the S pattern.

UV-C bulbs 306a-306d may extend parallel to axes 304a, 304c, 304e and 304g in chambers 302a, 302c, 302e and 302g respectively.

Figure 5:
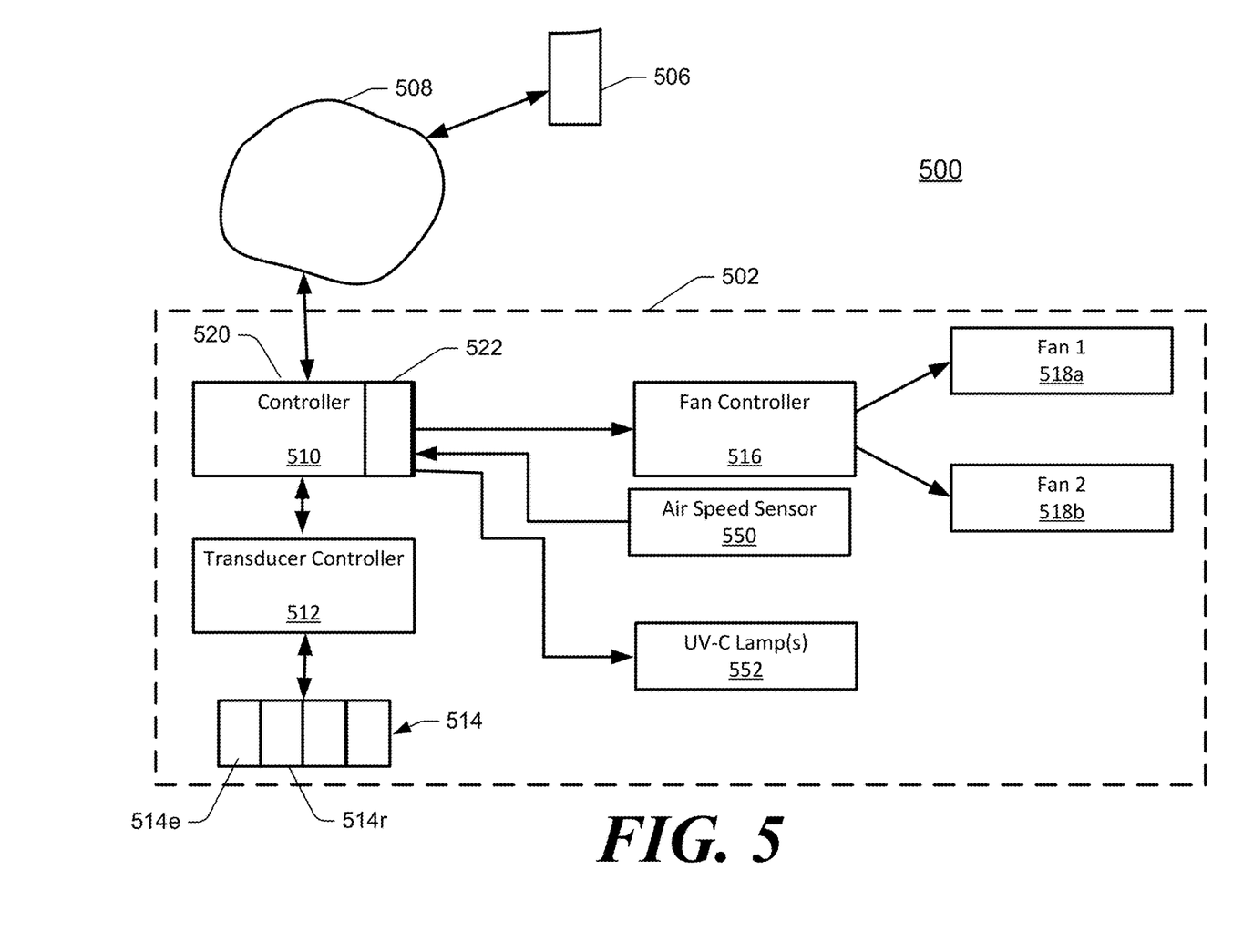
FIG. 5 is a schematic diagram of the air sterilizer device.

In FIG. 5, there is shown a simplified circuit diagram 500 for the air sterilizer device 502 (100 FIG. 1). The Air sterilizer device 502 may be coupled (hardwired or wirelessly) via a network 508, such as local area network, wide area network, or broadband network, to a server, remote personal assistant device, or smart phone device 506. Device 502 includes a controller 510 coupled via a transducer controller 512 to transducers emitter/receptor (514e and 514r) pairs 514. Controller 510 may also be coupled via fan controller 516 to fan one 518a and fan two 518b (Fans 108 and 114 in FIG. 1 respectively), air speed sensor 550 and UV-C lamps 552 (which may include a ballast controller). Operation of the controller 120 for the air sterilizer device 100 is described in more detail in FIG. 6.

Figure 6:
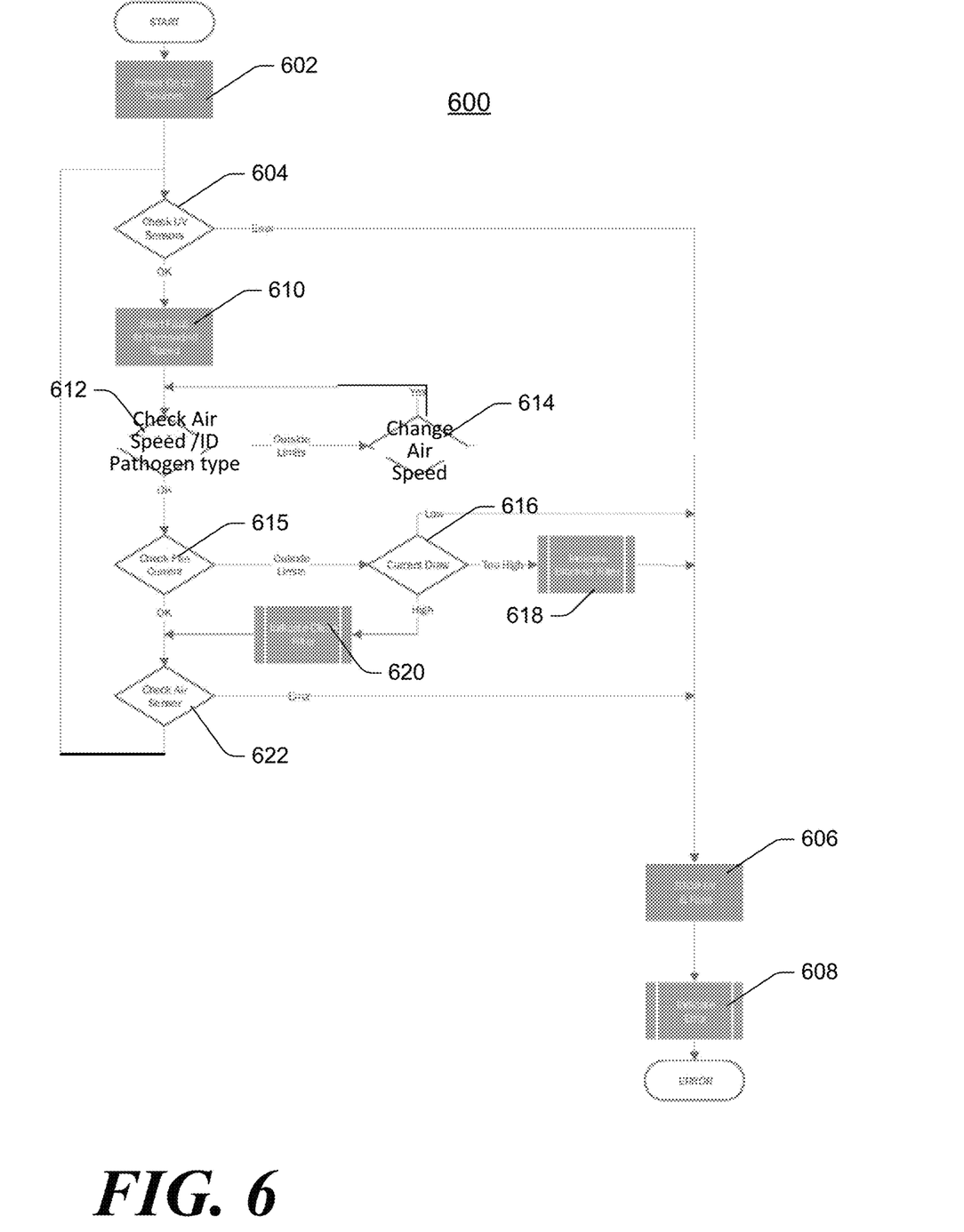
FIG. 6 illustrates a flow diagram of a process for using the air sterilization device to deactivate pathogens in the air.

Controller 510 (Computing Device 102 of FIG. 1 and 210 of FIG. 2) uses process 600 shown in FIG. 6. Controller 510 may include a processing device 520, memory 522, and interface hardware (not shown), which is connected to UV-C lamps 552 and transducer controller 512. Processing device 520 may include one or more microprocessors, microcontrollers or any such devices for accessing memory 522 or hardware. Processing device 520 has processing capabilities and memory 522 suitable to store and execute computer-executable instructions.

Processing device 520 executes instruction stored in memory 522, and in response thereto, processes signals (e.g., binary logic levels) from hardware. Hardware may include an input/output (I/O) device (not shown). I/O device may include a network and communication circuitry for communicating with network 508. I/O device may receive inputs from a user of the host computing device 508.

Memory 522 may include volatile and nonvolatile memory, removable and non-removable media implemented in any method or technology for storage of information, such as computer-readable instructions, data structures, program modules or other data. Such memory includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, RAID storage systems, or any other medium which can be used to store the desired information, and which can be accessed by a computer system.

Stored in memory 522 may be an application and a library of other applications including a database. The library may include preconfigured parameters (or set by the user before or after initial operation) such web site operating parameters, web site libraries, HTML (Hyper Text Markup Language) libraries, API's (Application program interface) and configurations.

Stored in the library in memory 522 (or received from external server 506) are the parameters regarding the pathogen patterns corresponding to patterns that may be sensed by transducer array 514 that indicate a pathogen type. Also stored in the library may be predetermined time periods necessary to turn on the lamps to destroy the pathogen type.

The exemplary process in FIG. 6 is illustrated as a collection of blocks in a logical flow diagram, which represents a sequence of operations that can be implemented in hardware, software, and a combination thereof. In the context of software, the blocks represent computer-executable instructions that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the process. For discussion purposes, the processes are described with reference to FIG. 5, although it may be implemented in other system architectures.

Referring to FIG. 6, a flowchart of process 600 performed by controller 510 when executing the software instructions in an application is shown. Process 600 includes blocks 602-618.

In the process 600 in block 602, all UV-C bulbs are turned on.

In block 604, light sensors located in each chamber 110 (FIG. 1) is checked by controller 510 to determine if the UV-C bulb is turned on.

If the UV-C bulb are not sensed as being turned on, in block 606 all bulbs and fans are turned off and an error indication is sent out by controller 510 (over the network, or through and audio/visual alarm) in block 608.

If the UV-C bulb is sensed as being turn on, the controller 510 in block 610 sets the fans to operate at a desired predetermined speed that causes air to flow through the chamber 110 at a predetermined flow rate that ensures the pathogen is irradiated by the UV-C bulbs for at least 3.2 seconds while passing through the chamber 110 to deactivate all known pathogens/viruses.

The controller 510 in block 612 checks the air speed by reading an air speed sensor, detecting fan revolutions per minute, checking current draw and/or identifying the pathogen type as previously described. If the air speed and/or identified pathogen type is determined to require greater or less flow rate by the fan(s), the air speed is changed in block 614 and then checked again in block 612. This air flow rate through the chamber 110 could be increased if only Covid-19 was detected as the time to deactivate Covid-19 is less, and the air flow rate through the chamber 110 could be decreased if a MRSA virus were detected as the time period under UV-C light to deactivate MRSA is longer. If no pathogens were detected the lamp could be turned off.

If the air speed and/or identified pathogen type is determined to be correct, then in block 615 the controller may check the fan current. If the current is outside of predetermined limits, in block 616, the controller 510 determines if the current draw is low or too high. If the current draw is too high, in block 618 and indication may be provided that a filter is block and needs to be changed, and the controller 510 then stops the bulbs and fans in block 606.

If the current draw is high, the controller 510 may send an indication in block 620 via the network 508 that a filter 106 needs to be changed.

In block 622, the controller 510 checks the air sensor and/or uv-c light sensor 118 to determine if it is working properly.

If the sensors 118 are not working properly, in block 606 the controller 510 then turns off the bulbs and stops the fans.

If the air sensors are working properly, the controller repeats block 604, checks a UV light sensor 118 located in each chamber 110 to determine if the UV-C bulb is turned on and then repeats blocks 606-622.

Figures 7A, 7B, 7C:
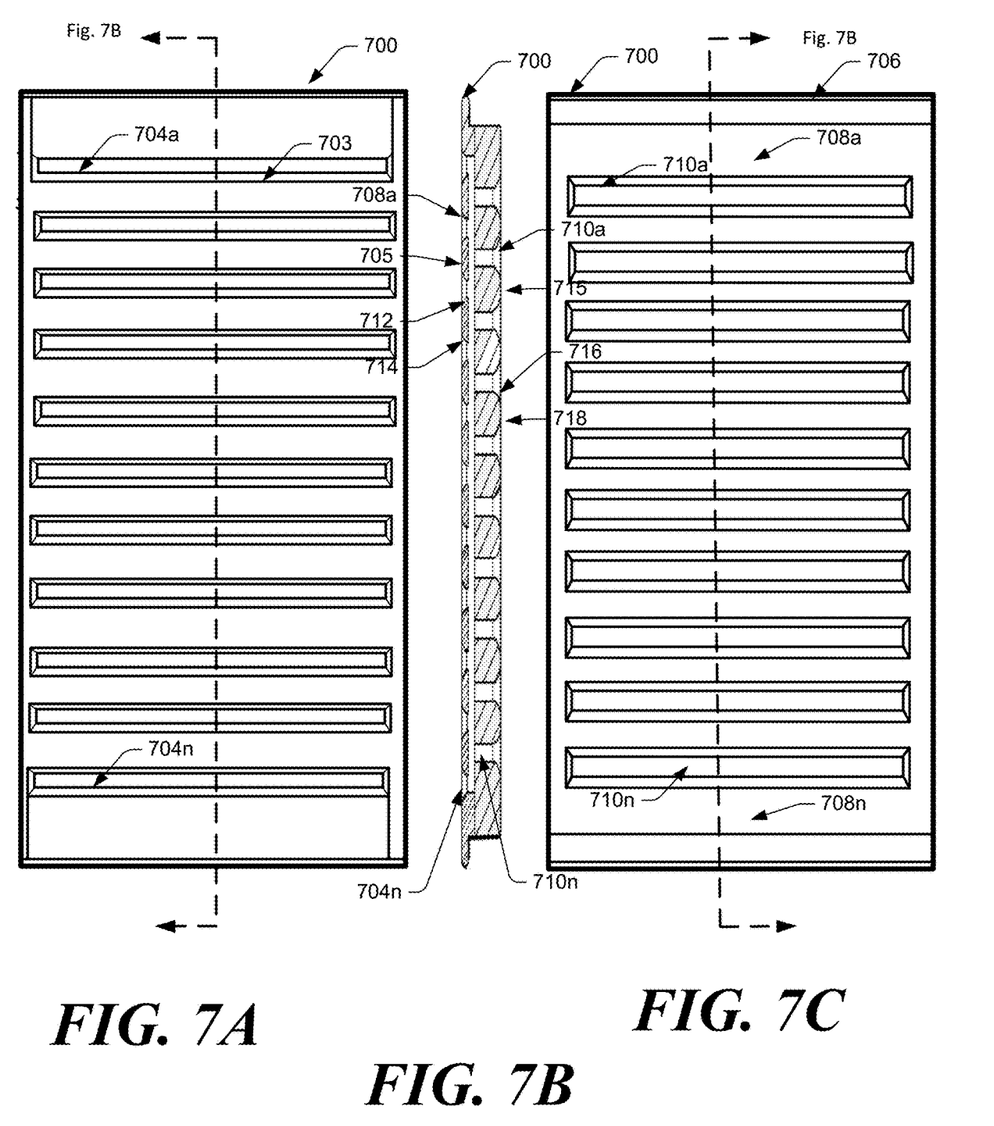
FIGS. 7A, 7B and 7C are top, side cross sectional and bottom plan views respectively of exemplary embodiments light blocking vents shown in FIG. 1 and FIG. 2.

Referring to FIGS. 7A-7C, then is shown an exemplary rectangular shaped light blocking vent 700. Although vent 700 is shown as a rectangular shape, vent 700 could be any geometric shape such as circular shape or triangular shape. Vent 700 has a top side 702 with cross bars 703 forming apertures 704a-n, and a bottom side 706 with a cross bars 708 forming apertures 710a-n. Apertures 704a-n are off set from apertures 710a-n as shown in FIG. 7B so that light does not directly pass-through vent 700. In additional cross bars 703 form tabs 705 with elongated portions 712 and 714 extending toward the bottom side at an angle of 32 degrees.

Cross bar 708 likewise form many elongated tabs 715 with elongated portions 716 and 718 extending toward top side at an angle of 32 degrees.

While the above detailed description has shown, described and identified several novel features of the invention as applied to a preferred embodiment, it will be understood that various omissions, substitutions and changes in the form and details of the described embodiments may be made by those skilled in the art without departing from the spirit of the invention. Accordingly, the scope of the invention should not be limited to the foregoing discussion but should be defined by the appended claims. While the above detailed description has shown, described and identified several novel features of the invention as applied to a preferred embodiment, it will be understood that various omissions, substitutions and changes in the form and details of the described embodiments may be made by those skilled in the art without departing from the spirit of the invention. Accordingly, the scope of the invention should not be limited to the foregoing discussion but should be defined by the appended claims.

What is claimed is:

1. An apparatus for irradiating pathogens in the air of an interior space, comprising:
    a housing containing inner walls that form an elongated chamber with a first end and a second end and enclose an axis extending along the elongated chamber parallel to the inner walls;
    an elongated ultraviolet-C (UV-C) light source extending within the elongated chamber from the elongated chamber first end to the elongated chamber second end parallel to the axis;
    a reflective coating applied to the inner walls of the elongated chamber to amplify UV-C light that emits from the elongated UV-light source extending within the elongated chamber;
    one or more fans to direct air from outside of the housing into the elongated chamber first end over the reflective coating and to direct air within the elongated chamber out of the elongated chamber second end to outside of the housing; and
    a controller to automatically adjust the speed of the one or more fans to ensure that the air passes through the elongated chamber and over the reflective coating at a predetermined flow rate such that pathogens in the air are irradiated in the elongated chamber for a sufficient time period to be deactivated by the ultraviolet-C light source,
    wherein the controller receives an indication of types of pathogens to be deactivated, and automatically sets the speed of the one or more fans based on the indication to ensure that the air passes through the elongated chamber over the reflective coating at one of a plurality of predetermined flow rates such that the type of pathogens in the air are irradiated in the elongated chamber for a sufficient time period to be deactivated by the ultraviolet-C light source.

2. The apparatus as recited in claim 1 further comprising:
    a plurality of vents disposed adjacent the elongated chamber first end and the elongated chamber second end for blocking light from the UV-C light source from exiting outside of the housing.

3. The apparatus as recited in claim 2 wherein one of the vents includes a plurality of slats having at least a portion positioned at an angle of 30-35 degrees with respect to the axis.

4. An apparatus for irradiating pathogens in the air of an interior space, comprising:
    a housing containing inner walls that form an elongated chamber with a first end and a second end and enclose an axis extending along the elongated chamber parallel to the inner walls;
    an elongated ultraviolet-C (UVC) light source extending within the elongated from the elongated chamber first end to the elongated chamber second end parallel to the axis;
    one or more fans to direct air from outside the housing into the elongated chamber first end and to direct air within the elongated chamber out of the elongated chamber second end to outside of the housing;
    a controller to adjust the power to the one or more fans to ensure that the air passes through the elongated chamber at a predetermined flow rate such that pathogens in the air are irradiated in the elongated chamber for a sufficient time period to be deactivated by the ultraviolet-C light source;
    a surface adjacent to an opening and through which air can pass over before entering the elongated chamber, and in which pathogens in the air can be deposited, the surface coupled with the housing and disposed adjacent to the elongated chamber first end; and
    an ultrasonic sensor to detect identifiable patterns of one or more pathogens passing and deposited on the surface, wherein the controller provides an indication of a pathogen type based on the detected pattern.

5. The apparatus as recited in claim 4 wherein the controller changes fan speed of the one or more fans based on the pathogen type detected.

6. The apparatus as recited in claim 1 further comprising:
    a sensor to detect a flow rate of air passing through the elongated chamber; and
    wherein the controller increases or decreases the fan speed of the one or more fans based on the detected air flow rate to ensure that pathogens in the air passing through the elongated chamber are irradiated by the UV-C light source for a sufficient time period to kill such pathogens.

7. The apparatus as recited in claim 1 further comprising wherein the controller sets the speed of the one or more fans to a predetermined revolutions per minute to ensure that air passes through the elongated chamber at a sufficient flow rate such that pathogens in said air are exposed to the UV-C light source for a sufficient time period to become deactivated.

8. The apparatus as recited in claim 1 further comprising:
    an air filter disposed in the outer housing adjacent the elongated chamber first end to filter air prior to entering the chamber.

9. A method for sterilizing pathogens in the air within an outer housing that supports an inner housing having inner walls that enclose an elongated chamber with a first end and a second end and enclose an axis extending along the elongated chamber parallel to the inner walls, the method comprising:
    directing, with one or more fans, air to pass from outside of the outer housing through the elongated chamber parallel to the axis via the elongated chamber first end and out of the elongated chamber to outside of the outer housing via the elongated chamber second end;
    irradiating, with an elongated ultraviolet-c (UV-C) light source extending within the elongated chamber parallel to the axis, air passing through the elongated chamber;

detecting an air flow rate of air passing through the elongated chamber;

determining one or more of a plurality of pathogen types present in air to be deactivated when passed through the elongated chamber; and setting the air flow rate based on the determined one or more of the plurality of pathogen types to be deactivated and by adjusting a speed of the one or more fans in response to the detected air flow rate to ensure that the determined one or more of the plurality of pathogen types in the air passing through the elongated chamber are irradiated by the UV-C light source for a sufficient time period to become deactivated.

10. The method as recited in claim 9 wherein the walls of the inner housing form a cylindrical tube with an inside surface, and wherein the method further comprises applying a reflective coating to inside surface of cylindrical tube.

11. The method as recited in claim 10 further comprising:
detecting with a sensor a flow rate of air passing through the elongated chamber; and increasing or decreasing fan speed based on the detected air flow rate to ensure that the determined pathogen in the air passing through the elongated chamber is irradiated by the UV-C light source for a sufficient time period to kill such pathogens.

12. A method for sterilizing pathogens in the air within an outer housing that supports an inner housing having inner walls that enclose an elongated chamber with a first end and a second end and enclose an axis extending along the elongated chamber parallel to the inner walls, the method comprising:

directing, with one or more fans, air to pass from outside of the outer housing through the elongated chamber parallel to the axis via the elongated chamber first end and out of the elongated chamber to outside of the outer housing via the elongated chamber second end;

irradiating, with an elongated ultraviolet-c (UV-C) light source extending within the elongated chamber parallel to the axis, air passing through the elongated chamber;

setting a speed of the one or more fans to ensure that pathogens in the air passing through the elongated chamber are irradiated by the UV-C light source for a sufficient time period to become deactivated;

disposing a surface adjacent an opening and adjacent the elongated chamber first end by which air can pass before entering the elongated chamber;

depositing one or more pathogens in the air on the surface prior to entering the chamber;

detecting with an ultrasonic sensor, patterns of one or more pathogens deposited on the surface; and sending a signal indicating a pathogen type based on the detected pattern.

13. The method as recited in claim 12, further comprising:
changing with a controller the speed of the one or more fans based on the pathogen type detected.

14. The method as recited in claim 9, wherein the flow rate of air passing through the elongated chamber is detected by determining a revolution speed of the one or more fans.

15. An apparatus for irradiating pathogens in the air comprising:

an outer housing supporting an inner housing having inner walls that form a first and a second elongated chamber, each elongated chamber having a first end and a second end, a first axis extending along the first elongated chamber parallel to the inner walls of the first elongated chamber and a second axis extending along the second elongated chamber parallel to the inner walls of the second elongated chamber, wherein the first elongated chamber second end couples with the second elongated chamber first end, and wherein the first axis extending through the first elongated chamber extends parallel to the second axis;

a reflective coating applied to the inner walls of at least one of the first elongated chamber and the second elongated chamber to amplify UV-C light emitting from at least one of the elongated UV-C light bulb extending within the first elongated chamber and the elongated UV-C light bulb extending within the second elongated chamber;

an elongated ultraviolet-c (UV-C) light bulb extending within the first elongated chamber parallel to the first axis and another elongated ultraviolet-C (UV-C) light bulb extending within the second elongated chamber parallel to the second axis;

at least one of a first fan to direct air from outside of the housing into the first elongated chamber first end and a second fan to direct air within the first and second elongated chambers out via the second elongated chamber and the second elongated chamber second end to outside of the housing, such that pathogens in the air are irradiated by the UV-C light bulbs when passing through the first and second elongated chambers;

a sensor to detect a flow rate of air passing through at least one of the first elongated chamber and the second elongated chamber; and a controller to increase or decrease a speed of at least one of the first fan and the second fan based on the detected air flow rate to ensure that pathogens in the air passing through at least one of the first elongated chamber and the second elongated chamber are irradiated by the UV-C light bulbs for a sufficient time period to kill such pathogens, wherein the controller receives an indication of types of pathogens to be deactivated, and automatically sets the speed of at least one of the first fan and the second fan based on the indication to ensure that the air passes through the elongated chamber over the reflective coating at one of a plurality of predetermined flow rates such that the type of pathogens in the air are irradiated in the elongated chamber for a sufficient time period to be deactivated by the ultraviolet-C light source.

16. The apparatus as recited in claim 15 wherein the inner walls that form the first and the second elongated chambers, respectively are shaped as a first cylindrical tube and a second cylindrical tube, and the reflective material coats inner walls of the first cylindrical tube and the second cylindrical tube.

17. The apparatus as recited in claim 4, wherein the surface includes a vent slat.

18. The apparatus as recited in claim 9 further comprising:
receiving an indication that another one of the plurality of pathogen types present in the air is to be deactivated when passed through the elongated chamber; and changing the air flow rate by adjusting the speed of the one or more fans in response to the detected flow rate of the air and in response to receiving another one of the plurality of pathogen types present in air is to be deactivated to ensure that the another one of the plurality of pathogen types in the air passing through the elongated chamber are irradiated by the UV-C light source for a sufficient time period to become deactivated.

* * * * *